United States Patent [19]

Fujii et al.

[11] Patent Number: 5,141,941
[45] Date of Patent: Aug. 25, 1992

[54] ARALKYLAMINE DERIVATIVES, AND FUNGICIDES CONTAINING THE SAME

[75] Inventors: Katsutoshi Fujii; Toshinobu Tanaka; Yasuhisa Fukuda, all of Ube, Japan

[73] Assignee: Ube Industries, Ltd., Yamaguchi, Japan

[21] Appl. No.: 437,341

[22] Filed: Nov. 15, 1989

[30] Foreign Application Priority Data

Nov. 21, 1988 [JP] Japan ................. 63-292444
Mar. 16, 1989 [JP] Japan ................... 1-62069
Aug. 2, 1989 [JP] Japan .................. 1-199207
Aug. 4, 1989 [JP] Japan .................. 1-201245

[51] Int. Cl.⁵ ............... C07D 239/47; C07D 239/42; C07D 401/12; A01N 43/54
[52] U.S. Cl. .................... 514/256; 514/259; 514/260; 514/258; 514/269; 514/272; 514/274; 514/275; 514/276; 544/317; 544/324; 544/323; 544/328; 544/329; 544/326; 544/278; 544/253; 544/260; 544/258; 544/269; 544/272; 544/274; 544/275; 544/276
[58] Field of Search ............... 544/317, 324, 323, 328, 544/329, 326, 278, 253, 286; 514/259, 269, 275

[56] References Cited

U.S. PATENT DOCUMENTS 2,437,683 3/1948 Curd et al. .............. 544/324

Primary Examiner—John M. Ford
Attorney, Agent, or Firm—Frishauf, Holtz, Goodman & Woodward

[57] ABSTRACT

Disclosed are a compound of the formula (I) or an acid addition salt thereof:

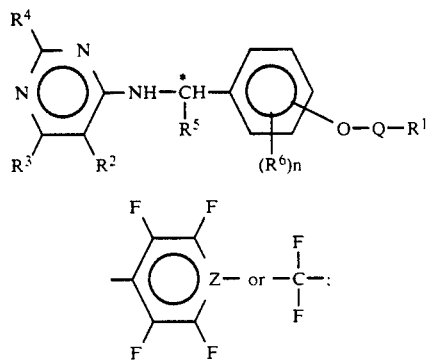

wherein Q represents $R^1$, $R^2$, $R^3$, $R^4$, $R^5$, $R^6$, n and z are defined as in the specification, preparation method thereof and fungicides containing the same.

36 Claims, No Drawings

ARALKYLAMINE DERIVATIVES, AND FUNGICIDES CONTAINING THE SAME

FIELD OF THE INVENTION

This invention relates to aralkylamine derivatives, processes for producing the same and fungicides containing the same as the active ingredient.

BACKGROUND OF THE INVENTION

There have been known in the art a large number of aralkylamine derivatives. For example, Journal of American Chemical Society (J. A. C. S) 80, 2189 (1958) discloses 4-benzylamino-6-chloropyrimidine as the diuretic intermediate, but no fungicidal activity was recognized in these compounds.

Also, Japanese Unexamined Patent Publications Nos. 36666/1984, 36667/1984, 42387/1984, 286373/1986, 67/1987, 225364/1988 and 68362/1989 disclose various aminopyrimidine derivatives. These compounds all have insecticidal, acaricidal and fungicidal activities, and are known to be effective against injurious insects, mites such as diamondback moth, aphid, citrus red mite, two-spotted spider mite, etc., and various injurious diseases in agriculture and horticulture such as rice blast, tomato late blight, tomato downy mildew, cucumber powdery mildew, etc. However, although these compounds have potent activities as insecticidal and acaridical agents, their activities as the fungicidal agent are not sufficient.

SUMMARY OF THE INVENTION

The present inventors have investigated intensively in order to obtain compounds having more excellent fungicidal activity than the above known compounds, and consequently found that the compounds represented by the following formula have markedly improved fungicidal activity to accomplish the present invention.

The present invention provides a compound of the formula: Formula (I)

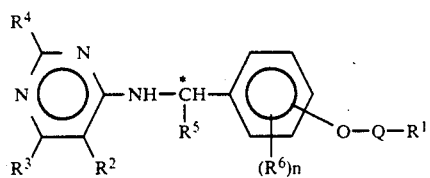

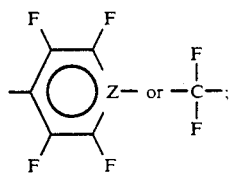

wherein Q represents $R^1$ represents hydrogen atom, a halogen atom, a halolower alkyl group, an alkanoyl group, nitro group, cyano group or 1,3-dioxoran-2-yl group when Q represents

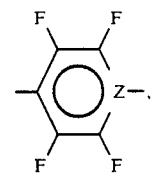

$R^1$ represents hydrogen atom or halogen atoms when Q represents —$CF_2$—; $R^2$ and $R^3$ each represent a halogen atom or a lower alkyl group, or $R^2$ and $R^3$ are fused together with the pyrimidine ring to which they are bonded to represent an unsaturated 5- or 6-membered ring which may also have one sulfur atom constituting the ring; $R^4$ represents hydrogen atom, a halogen atom, a lower alkyl group, a cycloalkyl group, a lower alkoxy group, a lower alkylthio group or an amino group which may be substituted with a lower alkyl; $R^5$ represents hydrogen atom, a lower alkyl group, a cycloalkyl group, a halo-lower alkyl group; $R^6$ represents hydrogen atom, a halogen atom, a lower alkyl group, a lower alkoxy group or a halo-lower alkoxy group; n represents an integer of 1 or 2; and Z represents carbon atom or nitrogen atom, an acid addition salt thereof, a process for preparing the same and fungicide containing said compound as the active ingredient.

In the above formula (I), as the halogen atom, fluorine, chlorine, bromine and iodine may be included.

As the alkanoyl group, formyl, acetyl, propionyl, butyryl, isobutyryl and valeryl and the like may be included.

As the halo-lower alkyl group, trifluoromethyl, difluoromethyl, 2-fluoromethyl and 2,2,2-trifluoroethyl and the like may be included.

As the lower alkyl group, straight chain or branched alkyl groups having 1 to 5 carbon atoms such as methyl, ethyl, propyl, isopropyl, butyl, isobutyl, sec-butyl, t-butyl, pentyl, isopentyl and neopentyl may be included.

As the cycloalkyl group, cycloalkyl groups having 3 to 6 carbon atoms such as cyclopropyl, cyclopentyl and cyclohexyl may be included.

As the lower alkoxy group, alkoxy groups having 1 to 5 carbon atoms such as methoxy, ethoxy, propoxy, isopropoxy, butoxy and pentyloxy may be included.

As the lower alkyothio group, an alkylthio group having 1 to 5 carbon atoms such as methylthio, ethylthio, propylthio, isopropylthio, butylthio, pentylthio and the like may be included.

As the halo-lower alkoxy group, a haloalkoxy group having 1 to 3 carbon atoms such as monofluoromethoxy, difluoromethoxy, trifluoromethoxy, bromodifluoromethoxy, 2-fluoroethoxy, 2,2-difluoroethoxy, 2,2,2-trifluoroethoxy, 3,3,3-trifluoropropoxy and the like may be included.

As the amino group which may be also substituted with lower alkyl, unsubstituted amino groups or amino groups substituted with 1 or 2 alkyl having 1 to 5 carbon atoms such as amino, monomethylamino, dimethylamino, monoethylamino, diethylamino, monopropylamino, dipropylamino, monobutylamino, dibutylamino, monopentylamino and dipentylamino and the like may be included.

As the =CH—$R^5$ group, —$CH_2$—, —CH($CH_3$)—, —CH($C_2H_5$)—, —CH(n—$C_3H_7$)—, —CH(i—$C_3H_7$)—,

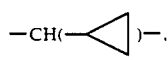

—CH(t—C$_4$H$_9$)—, —CH(n—C$_5$H$_{11}$)—, —CH(CF$_3$)—, —CH(CHF$_2$)—, —CH(CH$_2$F)—, —CH(CH$_2$CH$_2$F)— and —CH(CH$_2$CF$_3$)— may be included.

In the above formula (I), preferable groups are as follows.

As the pyrimidinyl group substituted with $R^2$, $R^3$ and $R^4$, for example, the following groups are preferred.

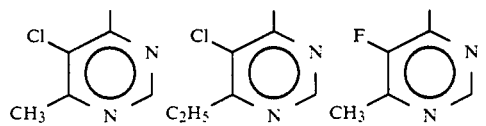
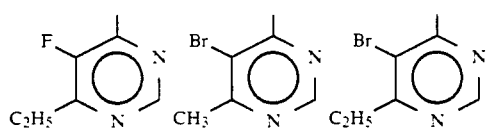
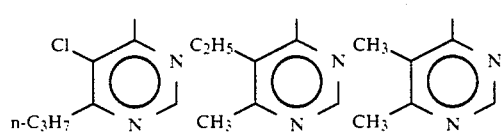
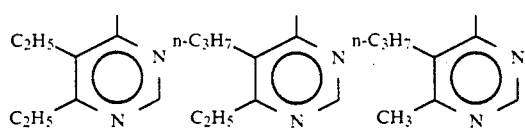
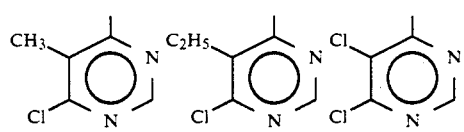
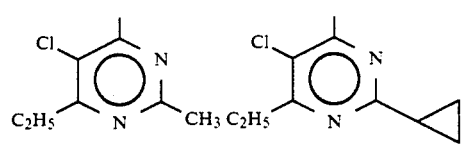
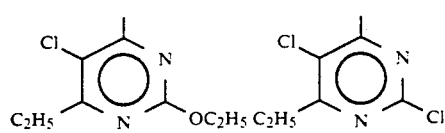

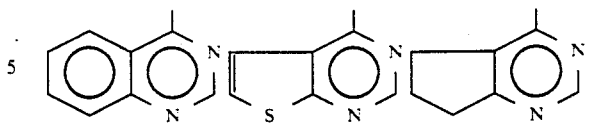

As $R^1$, hydrogen atom, fluorine atom, chlorine atom, bromine atom, difluoromethyl group, trifluoromethyl group and formyl group are preferred when Q is

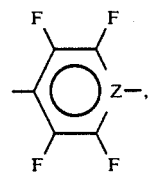

while hydrogen atom, fluorine atom, chlorine atom and bromine atom are preferred when Q is —CF$_2$—.

As $R^5$, methyl, ethyl, isopropyl and cyclopropyl groups are preferred.

Z is preferably carbon atom.

When Q is

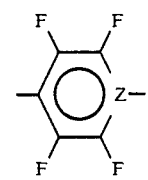

When Q is the substitution position thereon should be preferably at the 3-position or the 4-position relative to >CH—R$^5$. When Q is —CF$_2$—, it should be preferably at the 3- or 4-position relative to >CH—R$^5$.

$R^6$ is preferably hydrogen atom, fluorine atom, chlorine atom, methyl group, mothoxy group or difluoromethoxy group.

As can be understood from the above formula (I), the compound of the present invention has an amino group, forms readily an acid addition salt, and such salts are also included within the present invention.

As the acid for forming acid addition salt, there may be included, for example, inorganic acids such as hydrochloric acid, hydrobromic acid, nitric acid, sulfuric acid and phosphoric acid; carboxylic acids such as formic acid, oxalic acid, fumaric acid, adipic acid, stearic acid, oleic acid and aconitic acid; organic sulfonic acids such as methanesulfonic acid, benzenesulfonic acid and p-toluenesulfonic acid; and saccharin, etc. In the above formula (I), when the carbon atom with the mark * is asymmetric carbon, individual optical isomers and racemic compounds or mixtures of them are all included within the present invention.

Table 1 and Table 2 show examples of the compounds of the present invention, which are not limitative of the present invention.

TABLE 1

(I')

[Structure: R⁴, R³, R² substituted pyrimidine-NH-CH(R⁵)-phenyl(R⁶)ₙ-O-tetrafluorophenyl-Z-R¹]

| Compound No. | [pyrimidine with R², R³, R⁴] | R⁵ | (R⁶)n | —O—[tetrafluorophenyl]—Z—R¹ | Physical property |
|---|---|---|---|---|---|
| 1 | [5-Cl, 4-CH₃, 6-C₂H₅ pyrimidine] | $C_2H_5$ | H | 4-O—[C₆F₄]—F | m.p. 57~59° C. |
| 2 | " | " | " | 4-O—[C₆F₄]—CF₃ | m.p. 58~61° C. |
| 3 | " | " | " | 4-O—[C₆F₄]—CN | $n_D^{24.4}$ 1.5677 |
| 4 | " | " | " | 4-O—[C₆F₄]—CHO | $n_D^{24.4}$ 1.5734 |
| 5 | " | " | " | 4-O—[C₆F₄]—NO₂ | $n_D^{24.4}$ 1.5712 |
| 6 | " | " | " | 4-O—[C₆F₄]—COCH₃ | $n_D^{24.4}$ 1.5592 |
| 7 | " | " | " | 4-O—[tetrafluoropyridyl] | $n_D^{24.4}$ 1.5562 |

TABLE 1-continued

Structure (I'):
R⁴-pyrimidine-NH-CH(R⁵)-phenyl(R⁶)n-O-C₆F₄-Z-R¹

| Compound No. | R²/R³/R⁴ pyrimidine | R⁵ | (R⁶)n | –O–Ar–Z–R¹ | Physical property |
|---|---|---|---|---|---|
| 8 | " | " | " | 4-O-C₆F₄-CH(OCH₂CH₂O) (1,3-dioxolane) | $n_D^{24.4}$ 1.5589 |
| 9 | 5-Cl, 4-CH₃, 6-C₂H₅ pyrimidine | CH₃ | " | 4-O-C₆F₄-F | m.p. 88~89° C. |
| 10 | " | i-C₃H₇ | " | " | $n_D^{24.2}$ 1.5401 |
| 11 | 5-Cl, 4-CH₃, 6-CH₃ pyrimidine (with C₂H₅?) | C₂H₅ | H | 4-O-C₆F₄-F | m.p. 118~121° C. |
| 12 | 5-CH₃, 6-Cl pyrimidine | " | " | " | m.p. 120~125° C. |
| 13 | quinazoline | " | " | " | m.p. 172~176° C. |
| 14 | thieno[2,3-d]pyrimidine | " | " | " | m.p. 155~157° C. |
| 15 | quinazoline | CH₃ | " | " | m.p. 144~148° C. |

TABLE 1-continued

Structure (I'):

R⁴-pyrimidine-NH-CH(R⁵)-phenyl(1,2,3,4,5,6 positions with (R⁶)n)-O-C₆F₄-Z-R¹

| Compound No. | R², R³, R⁴ (pyrimidine) | R⁵ | (R⁶)n | -O-C₆F₄-Z-R¹ | Physical property |
|---|---|---|---|---|---|
| 16 | 5-Cl, 6-C₂H₅ pyrimidine | H | " | 3-O-C₆F₄ | m.p. 114~115° C. |
| 17 | 5-Cl, 6-CH₃ pyrimidine | " | " | 4-O-C₆F₄ | m.p. 110~115° C. |
| 18 | 5-CH₃, 6-Cl pyrimidine | " | " | " | m.p. 128~132° C. |
| 19 | quinazoline | H | " | 4-O-C₆F₄ | m.p. 164~167° C. |
| 20 | thieno[2,3-d]pyrimidine | " | " | " | m.p. 126~130° C. |
| 21 | 5-Cl, 6-C₂H₅ pyrimidine | CH₃ | " | 3-O-C₆F₄ | $n_D^{24.4}$ 1.5522 |
| 22 | 5-Cl, 6-Cl pyrimidine | C₂H₅ | H | 4-O-C₆F₄ | m.p. 94~96° C. |

TABLE 1-continued

Structure (I'):

R⁴-pyrimidine-NH-CH(R⁵)-phenyl(R⁶)n-O-C₆F₄-Z-R¹

| Compound No. | $\begin{matrix}R^2\\R^3\end{matrix}$ pyrimidine $R^4$ | R⁵ | (R⁶)n | —O—C₆F₄—Z—R¹ | Physical property |
|---|---|---|---|---|---|
| 23 | thieno[2,3-d]pyrimidine (R⁴=CH₃) | CH₃ | " | " | m.p. 158~161° C. |
| 24 | R²=Cl, R³=CH₃, R⁴=CH₃ | " | " | " | m.p. 90~91° C. |
| 25 | " | " | " | 3-O-C₆F₄-F | $n_D^{21.6}$ 1.5580 |
| 26 | R²=Br, R³=C₂H₅, R⁴=CH₃ | C₂H₅ | " | 4-O-C₆F₄-F | m.p. 86~88° C. |
| 27 | R²=Br, R³=CH₃, R⁴=CH₃ | " | " | " | m.p. 93~96° C. |
| 28 | R²=Cl, R³=n-C₃H₇, R⁴=CH₃ | CH₃ | " | " | m.p. 62~65° C. |
| 29 | R²=F, R³=CH₃, R⁴=CH₃ | CH₃ | " | 4-O-C₆F₄-F | m.p. 117~119° C. |
| 30 | R²=Cl, R³=C₂H₅, R⁴=Cl | " | " | " | m.p. 74~77° C. |

TABLE 1-continued (I')

Structure: R4-pyrimidine-NH-CH(R5)-phenyl(R6)n-O-C6F4-Z-R1

| Compound No. | R²/R³/R⁴ (pyrimidine) | R⁵ | (R⁶)n | -O-C₆F₄-Z-R¹ | Physical property |
|---|---|---|---|---|---|
| 31 | R²=C₂H₅, R³=Cl, R⁴=CH₂N(CH₃)₂ (with CH₃) | C₂H₅ | " | " | m.p. 73~74° C. |
| 32 | R²=C₂H₅, R³=Cl, R⁴=OC₂H₅ (with CH₃) | " | " | 4-O-C₆F₄-OC₂H₅ | $n_D^{22.8}$ 1.5512 |
| 33 | R²=C₂H₅, R³=Cl (with CH₃) | " | " | 4-O-C₆F₄-CHF₂ | $n_D^{22.8}$ 1.5454 |
| 34 | R²=CH₃, R³=Cl (with CH₃) | " | " | 4-O-C₆F₄-Cl | m.p. 106~107° C. |
| 35 | " | " | " | 4-O-C₆F₄ (H) | m.p. 89~90° C. |
| 36 | " | cyclopropyl | " | " | Note 1 |
| 37 | R²=CH₃, R³=F (with CH₃) | C₂H₅ | " | 4-O-C₆F₄-F | $n_D^{26.4}$ 1.5400 |
| 38 | R²=C₂H₅, R³=CH₃ (with CH₃) | " | " | " | |

TABLE 1-continued

Structure (I'):
R⁴-pyrimidine-NH-CH(R⁵)-[phenyl(R⁶)n]-O-[tetrafluorophenyl]-Z-R¹

| Compound No. | R²,R³,R⁴ (pyrimidine) | R⁵ | (R⁶)n | —O—[C₆F₄]—Z—R¹ | Physical property |
|---|---|---|---|---|---|
| 39 | R²=C₂H₅, R³=C₂H₅, 4-methyl pyrimidine | C₂H₅ | " | 4-O-(tetrafluorophenyl)-F | |
| 40 | R²=n-C₃H₇, R³=C₂H₅, 4-methyl pyrimidine | " | " | " | |
| 41 | R²=F, R³=C₂H₅, 4-methyl pyrimidine | CH₃ | " | " | m.p. 88~91° C. |
| 42 | R²=Cl, R³=C₂H₅, 4-methyl, 2-CH₃ pyrimidine | C₂H₅ | " | " | $n_D^{26.4}$ 1.5466 |
| 43 | R²=Cl, R³=C₂H₅, 4-methyl, 2-cyclopropyl pyrimidine | " | " | " | |

Note 1:
(CDCl₃, δ ppm)
0.4~1.0(5H, m), 2.49(3H, s), 4.70(1H, dd), 5.82(1H, d),
6.80~7.40(5H, m), 8.30(1H, s)

TABLE 2

$$\text{R}^4\text{-pyrimidine-NH-CH(R}^5\text{)-phenyl(R}^6)_n\text{-O-CF}_2\text{-R}^1 \quad (I'')$$

| Compound No. | R², R³, R⁴ (pyrimidine) | R₅ | (R⁶)n | R¹ | Substitution position of —O—CF₂—R¹ | Physical property |
|---|---|---|---|---|---|---|
| 44 | 5-Cl, 4-CH₃, 6-C₂H₅ | C₂H₅ | H | F | 4 | Refer to Example 16 |
| 45 | " | " | " | Br | " | Refer to Example 17 |
| 46 | " | " | " | H | " | $N_D^{23.0}$ 1.5487 |
| 47 | 5-Cl, 4-CH₃, 6-CH₃ | " | " | " | " | $N_D^{24.4}$ 1.5471 |
| 48 | " | " | " | Br | " | |
| 49 | " | " | " | F | " | |
| 50 | " | " | " | Cl | " | |
| 51 | 5-Cl, 4-CH₃, 6-n-C₃H₇ | CH₃ | " | H | " | $N_D^{26.0}$ 1.5407 |
| 52 | " | C₂H₅ | " | " | " | $N_D^{30.0}$ 1.5298 |
| 53 | 5-F, 4-CH₃, 6-C₂H₅ | CH₃ | " | " | " | $N_D^{24.0}$ 1.5251 |
| 54 | 5-CH₃, 4-CH₃, 6-C₂H₅ | " | " | " | " | |
| 55 | 5-C₂H₅, 4-CH₃, 6-C₂H₅ | CH₃ | H | H | 4 | m.p. 76.5~79° |
| 56 | 5-n-C₃H₇, 4-CH₃, 6-C₂H₅ | " | " | " | " | |

TABLE 2-continued (I''')

Structure: R⁴-pyrimidine-NH-CH(R⁵)-phenyl(R⁶)ₙ-O-CF₂-R¹ (with R², R³ on pyrimidine)

| Compound No. | R², R³, R⁴ (pyrimidine) | R₅ | (R⁶)n | R¹ | Substitution position of —O—CF₂—R¹ | Physical property |
|---|---|---|---|---|---|---|
| 57 | 5-Cl, 6-C₂H₅, 4-CH₃, 2-CH₃ pyrimidine | '' | '' | '' | '' | $N_D^{27.2}$ 1.5120 |
| 58 | 5-Cl, 6-C₂H₅, 4-CH₃, 2-C₂H₅ pyrimidine | | | '' | '' | |
| 59 | 5-Cl, 6-C₂H₅, 4-CH₃, 2-cyclopropyl pyrimidine | | | | | |
| 60 | 5-Cl, 4-CH₃, 6-CH₃ pyrimidine | CF₃ | '' | '' | '' | |
| 61 | '' | cyclopropyl | '' | '' | '' | $N_D^{23.4}$ 1.5576 |
| 62 | '' | CH(CH₃)₂ | '' | '' | '' | $N_D^{26.0}$ 1.5378 |
| 63 | quinazoline (4-CH₃) | CH₃ | '' | '' | '' | |
| 64 | thieno[2,3-d]pyrimidine (4-CH₃) | '' | '' | '' | '' | m.p. 145° |
| 65 | 5-CH₃, 4-CH₃, 6-Cl pyrimidine | '' | '' | '' | '' | |

TABLE 2-continued (I'')

Structure: pyrimidine (with R4 at 2-position, R2 and R3 at 5,6-positions) — NH—CH(R5)—phenyl(R6)n—O—CF2—R1

| Compound No. | R² / R³ / R⁴ (pyrimidine) | R₅ | (R⁶)n | R¹ | Substitution position of —O—CF₂—R¹ | Physical property |
|---|---|---|---|---|---|---|
| 66 | 5-Cl, 4-CH₃, 2-CH₃ pyrimidine | CH₃ | H | H | 4 | m.p. 56~58° |
| 67 | 5-Cl, 4-CH₃, 2-C₂H₅ pyrimidine | " | " | " | " | $N_D^{30.0}$ 1.5442 |
| 68 | 5-Br, 4-CH₃, 2-C₂H₅ pyrimidine | " | " | " | " | $N_D^{28.0}$ 1.5358 |
| 69 | quinazoline (4-position) | C₂H₅ | " | " | " | m.p. 114~116° |
| 70 | thieno[2,3-d]pyrimidine | " | " | " | " | $N_D^{27.8}$ 1.6058 |
| 71 | cyclopenta-fused pyrimidine | CH₃ | " | " | " | m.p. 125.0~128.5° |
| 72 | 5,6-diCl, 4-CH₃ pyrimidine | " | " | " | " | $N_D^{24.0}$ 1.5566 |
| 73 | 5-Cl, 6-CH₃, 4-CH₃ pyrimidine | " | 3,5-(CH₃)₂ | " | " | $N_D^{25.0}$ 1.5510 |
| 74 | 5-Cl, 6-C₂H₅, 4-CH₃ pyrimidine | " | " | " | " | $N_D^{24.0}$ 1.5256 |
| 75 | " | " | " | 3-Cl | " | " | $N_D^{26.0}$ 1.5397 |

TABLE 2-continued $$(I''')$$

Structure: R⁴ and N on pyrimidine, NH—CH(R⁵)—phenyl(R⁶)ₙ—O—CF₂—R¹, with R³, R² on pyrimidine.

| Compound No. | R²/R³/R⁴ (pyrimidine) | R₅ | (R⁶)n | R¹ | Substitution position of —O—CF₂—R¹ | Physical property |
|---|---|---|---|---|---|---|
| 76 | 5-Cl, 4-CH₃, 6-CH₃ pyrimidine | " | " | " | " | $N_D^{24.6}$ 1.5536 |
| 77 | 5-Cl, 4-CH₃, 6-CH₃ pyrimidine | H | H | H | 4 | m.p. 71.0~72.4° |
| 78 | 5-Cl, 4-CH₃, 6-C₂H₅ pyrimidine | " | " | " | " | m.p. 69.5~71.5° |
| 79 | " | CH₃ | 3-CH₃ | " | " | $N_D^{26.2}$ 1.5392 |
| 80 | 5-Cl, 4-CH₃, 6-C₂H₅, 2-C₂H₅ pyrimidine | C₂H₅ | H | " | " | $N_D^{26.0}$ 1.5244 |
| 81 | 5-Cl, 4-CH₃, 6-C₂H₅, 2-cyclopropyl pyrimidine | " | " | " | " | $N_D^{26.4}$ 1.5812 |
| 82 | 5-Cl, 4-CH₃, 6-C₂H₅ pyrimidine | CH₃ | 3-F | " | " | $N_D^{25.6}$ 1.5236 |
| 83 | 4-CH₃, 6-CH₃, 2-SC₂H₅ pyrimidine | C₂H₅ | H | " | " | $N_D^{25.6}$ 1.5619 |
| 84 | 5-CH₃, 4-CH₃ thieno[2,3-d]pyrimidine | " | " | " | " | $N_D^{25.4}$ 1.5912 |

TABLE 2-continued

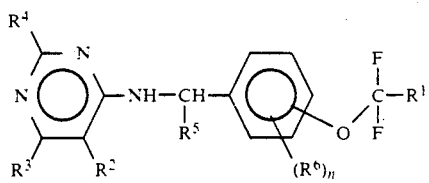

| Compound No. | R², R³, R⁴ | R₅ | (R⁶)n | R¹ | Substitution position of $-O-CF_2-R^1$ | Physical property |
|---|---|---|---|---|---|---|
| 85 | Cl, CH₃, CH₃ (pyrimidine) | CH₃ | 3-CH₃O | " | " | $N_D^{24.0}$ 1.5498 |
| 86 | Cl, C₂H₅, CH₃ (pyrimidine) | " | " | " | " | $N_D^{24.0}$ 1.5458 |
| 87 | " | cyclopropyl | H | " | " | $N_D^{23.6}$ 1.5582 |
| 88 | F-quinazoline, CH₃ | C₂H₅ | " | " | " | m.p. 127~130° |
| 89 | Cl, CH₃, CH₃ (pyrimidine) | CH(CH₃)₂ | 3-CH₃ | H | 4 | $N_D^{25.2}$ 1.5383 |
| 90 | " | CH₃ | 2-F | " | " | $N_D^{25.2}$ 1.5406 |
| 91 | Cl, C₂H₅, CH₃ (pyrimidine) | " | " | " | " | $N_D^{25.6}$ 1.5343 |
| 92 | n-C₃H₇, Cl, CH₃ (pyrimidine) | C₂H₅ | H | " | " | m.p. 55~57.5° |
| 93 | n-C₄H₉, Cl, CH₃ (pyrimidine) | " | " | " | " | $N_D^{26.6}$ 1.5380 |
| 94 | n-C₄H₉, Cl, CH₃, NH₂ (pyrimidine) | H | " | " | " | |

TABLE 2-continued (I''')

Structure: R⁴ pyrimidine–NH–CH(R⁵)–phenyl(R⁶)ₙ–O–CF₂–R¹ with R², R³ on pyrimidine

| Compound No. | R²,R³,R⁴ (pyrimidine) | R₅ | (R⁶)ₙ | R¹ | Substitution position of —O—CF₂—R¹ | Physical property |
|---|---|---|---|---|---|---|
| 95 | R²=n-C₄H₉, R³=CH₃, R⁴=N(CH₃)₂ (with CH₃ on ring) | " | " | " | " | $N_D^{21.8}$ 1.5456 |
| 96 | R²=Cl, R³=CH₃ (with CH₃ on ring) | CH₃ | " | " | 3 | $N_D^{23.2}$ 1.5538 |
| 97 | R²=Cl, R³=C₂H₅ (with CH₃ on ring) | " | " | " | " | $N_D^{23.2}$ 1.5471 |
| 98 | R³=CH₃, R⁴=SC₂H₅ (with CH₃ on ring) | C₂H₅ | " | " | 4 | $N_D^{26.6}$ 1.5584 |
| 99 | R²=Cl, R³=CH₃ (with CH₃ on ring) | CH₃ | 3-C₂H₅O | H | 4 | |
| 100 | R²=Cl, R³=C₂H₅ (with CH₃ on ring) | " | " | " | " | |
| 101 | R²=Cl, R³=CH₃ (with CH₃ on ring) | " | 3-CHF₂O | " | " | $N_D^{24.8}$ 1.5246 |
| 102 | R²=Cl, R³=C₂H₅ (with CH₃ on ring) | " | " | " | " | $N_D^{24.8}$ 1.5218 |
| 103 | R²=Cl, R³=CH₃ (with CH₃ on ring) | C₂H₅ | " | " | " | |

TABLE 2-continued (I''')

| Compound No. | | R5 | (R6)n | R1 | Substitution position of —O—CF2—R1 | Physical property |
|---|---|---|---|---|---|---|
| 104 | 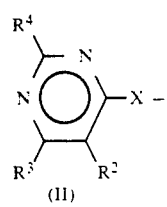 | " | " | " | " | |

The compound (I) of the present invention can be easily prepared according to a process which is known per se as shown below.

Preparation process A

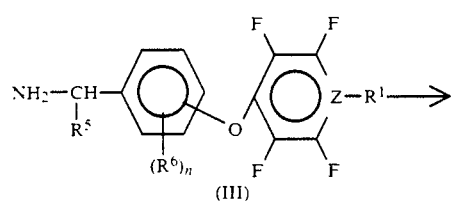

Preparation process A'

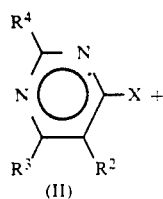

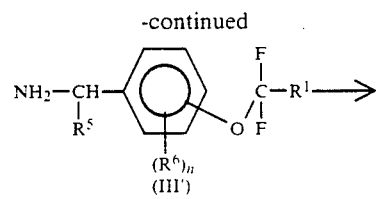

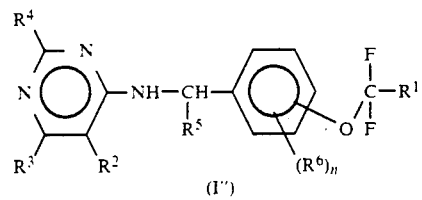

(wherein $R^1$, $R^2$, $R^3$, $R^4$, $R^5$, $R^6$, n and Z have the same meanings as defined above, and X represents an eliminable group).

This reaction is known per se, and the eliminable group X is not limited at all, but may include, for example, halogen atoms such as chlorine, bromine or iodine; alkylthio groups such as methylthio, ethylthio, propylthio and butylthio; alkanesulfonyloxy groups which may be also substituted with halogen such as methanesulfonyloxy, ethanesulfonyloxy and trifluoromethane-sulfonyloxy; arylsulfonyloxy groups such as benzene-sulfonyloxy and p-toluenesulfonyloxy, etc. and hydroxyl group and others.

As is apparent from the above reaction scheme, since the compound H-X is eliminated in the present reaction, in order to permit the reaction to proceed smoothly by trapping this, it is preferable to carry out the reaction in the presence of a base. The reaction is generally carried out in the presence of a solvent, but it is also possible to carry out the reaction by heating and melting the compounds of the formula (II) and the formula (III) or (III').

The solvent is not particularly limited, provided that it does not participate in the present reaction, and may include, for example, aromatic, aliphatic and alicyclic hydrocarbons which are chlorinated or not, such as benzene, toluene, xylene, methylnaphthalene, petroleum ether, ligroin, hexane, chlorobenzene, dichlorobenzene, methylene chloride, chloroform, dichloroethane, trichloroethylene and cyclohexane; ethers such as

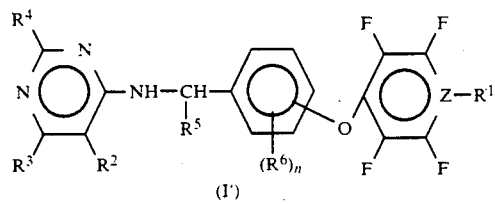

diethyl ether, dimethyl ether, tetrahydrofuran and dioxane; ketones such as acetone and methyl ethyl ketone; alcohols such as methanol, ethanol and ethylene glycol or hydrates thereof; amides such as N,N-dimethylformaldehyde (DMF) and N,N-dimethylacetamide; organic bases such as pyridine and N,N-diethylaniline; 1,3-dimethyl-2-imidazolidinone (DMI); dimethyl sulfoxide (DMSO) and mixtures of the above solvents, etc.

As the base, there may be included organic bases such as triethylamine, pyridine and N,N-diethylaniline, alkali metal alkoxides such as sodium methoxide and sodium ethoxide, inorganic bases such as sodium hydride, sodium amide, sodium hydroxide, potassium hydroxide, sodium carbonate and potassium carbonate, etc.

Also, for increasing the reaction rate, it is preferable to add 4-(N,N-dimethylamino)pyridine as the catalyst.

The reaction temperature is not particularly limited, but generally room temperature or higher and not higher than the boiling point of the solvent used, and it is preferable to heat the reaction mixture for shortening the reaction time.

Preparation process B

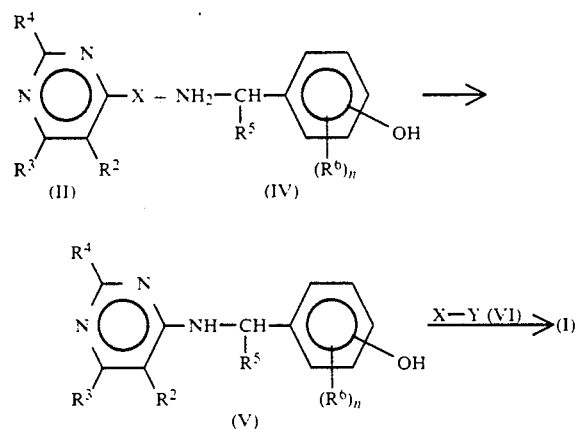

Preparation process B'

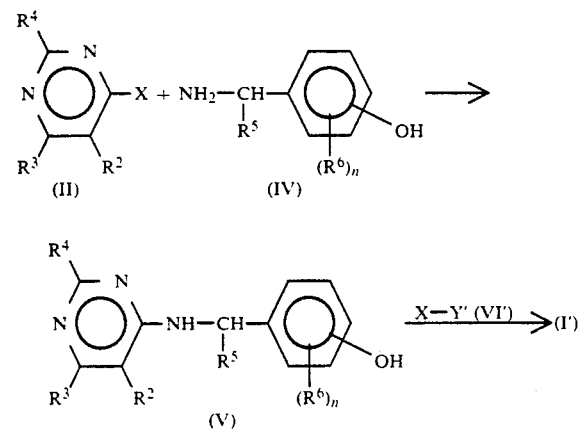

(wherein Y represents

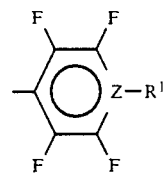

Y' represents

$R^1$, $R^2$, $R^3$, $R^4$, $R^5$, $R^6$, n and Z have the same meanings as defined above).

This process is a method in which the intermediate (V) is synthesized and then reacted with the compound (VI) or (VI'). As the solvent, the base, etc. to be used in this process, those as described in the above preparation processes A and A' can be suitably used.

In the above preparation processes A, A', B and B', the compounds of the formulae (III), (III') and (IV) to be used as the starting materials can be also prepared by, for example, the processes known per se as shown below.

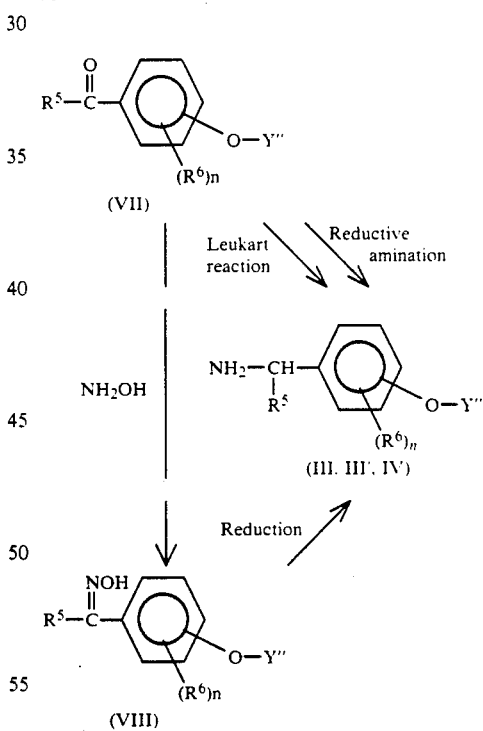

(wherein $R^5$, $R^6$ and n represents the same meaning as defined above; Y''' represents the same meaning as Y or Y' as defined above or hydrogen atom).

The compounds of the formula (I) obtained according to the respective processes can be purified suitably according to known means such as recrystallization, various chromatographies, etc.

The acid addition salt can be easily obtained by, for example, introducing an acid into the reaction mixture after completion of the reaction, and then removing the solvent.

The compound of the present invention is very effective for barley powdery mildew and wheat brown rust, and otherwise useful as the fungicide for agriculture and horticulture such as rice blast, cucumber downy mildew, tomato late blight, etc.

Also, the compound of the present invention is effective for agricultural and horticultural injurious insects such as planthoppers, leafhoppers, aphids, whiteflies, diamondback moth, etc., and otherwise also exhibits activity against citrus red mite, two-spotted spider mite, etc.

Thus, the uses, application fields of the compound of the present invention are very wide, high in activity and can be provided for practical application in various dosage forms.

The fungicide of the present invention contains one kind or two or more kinds of the compound of the formula (I) as the active ingredient.

The compound of the formula (I) may be also used as such, but generally formulated with carrier, surfactant, dispersing agent and auxiliary agent to prepare a composition such as powder, emulsion, fine particle, granule, wettable agent or oily suspension, aerosol, etc. before use.

Examples of preferable carrier may include solid carrier such as talc, bentonite, clay, kaolin, diatomaceous earth, white carbon, vermicullite, slaked lime, siliceous sand, ammonium sulfate and urea; liquid carriers including hydrocarbons such as kerosine and mineral oil, aromatic hydrocarbons such as benzene, xylene and toluene, chlorinated hydrocarbons such as chloroform and carbon tetrachloride, ethers such as dioxane and tetrahydrofuran, ketones such as acetone, cyclohexanone and isophorone, esters such as ethyl acetate, ethylene glycol acetate and dibutyl maleate, alcohols such as methanol, n-hexanol and ethylene glycol, polar solvents such as dimethylformamide and dimethyl sulfoxide, water or the like. As the gas phase carrier, mixed jetting can be also effected by use of air, nitrogen, carbon dioxide, Freon, etc.

As the surfactant or dispersing agent for effecting improvement of attachment and absorption of the present agent onto animals and vegetables, improvement of performances such as dispersion, emulsification and spreading of the drug, for example, alcohol, sulfuric acid esters, alkylsulfonic acid salts, ligninsulfonic acid salts, polyoxyethylene glycol ether, etc. may be employed.

Further, for improving the properties of the preparation, as the auxiliary agent, for example, carboxymethyl cellulose, polyethylene glycol, gum arabic, etc. may be employed.

The above-mentioned carrier, surfactant, dispersing agent and auxiliary agent may be employed individually alone or in combination depending on the respective purposes.

The active ingredient concentration when the compound of the present invention is formed into a preparation may be generally 1 to 50% by weight for emulsion, generally 0.3 to 25% by weight for powder, generally 1 to 90% by weight for wettable agent, generally 0.5 to 5% by weight for granule, generally 0.5 to 5% by weight for oil agent, generally 0.1 to 5% by weight for aerosol.

These preparations are diluted to appropriate concentrations, and can be provided for various uses by spraying on the vegetable stalk and leave, solid, water surface of a paddle field, or by way of direct application.

The present invention is described below in more detail by referring to Examples, but these Examples are not limitative of the scope of the present invention at all.

EXAMPLE 1

Synthesis of dl-5-chloro-6-ethyl-4-($\alpha$-ethyl-4-pentafluorophenoxybenzylamino)pyrimidine:

A mixture of 0.3 g of potassium hydroxide and 30 ml of dimethyl sulfoxide was heated under stirring at 100° C. for 30 minutes, then cooled to 50° C., and 1 g of dl-5-chloro-6-ethyl-4-($\alpha$-ethyl-4-hydroxybenzylamino) pyrimidine was added, followed by stirring for 30 minutes. To this solution was added 1 g of hexafluorobenzene, and the reaction was carried out at 70 C for 8 hours. After completion of the reaction, the reaction mixture was poured into water, and extracted with toluene. The extract was washed with water, dried over anhydrous sodium sulfate and then toluene was evaporated under reduced pressure. The oily product obtained was isolated by column chromatography (Wako gel C-200, eluted with toluene:ethyl acetate=10:1) to give 1 g of the desired product as colorless crystals.
m.p. 57°-59° C.

EXAMPLE 2

Synthesis of dl-5-chloro-6-ethyl-4-{$\alpha$-ethyl-4-(4-cyano-2,3,5,6-tetrafluorophenoxy) benzylamino}pyrimidine:

A mixture of 0.76 g of dl-5-chloro-6-ethyl-4-($\alpha$ethyl-4-hydroxybenzylamino)pyrimidine, 0.5 g of pentafluorobenzonitrile, 0.4 g of anhydrous potassium carbonate and 20 ml of 1,3-dimethyl-2-imidazolidinone (DMI) was heated under stirring at 70 .C for 8 hours. After completion of the reaction, the reaction mixture was poured into water, and extracted with toluene. The extract was washed with water, dried over anhydrous sodium sulfate and then toluene was evaporated under reduced pressure. The oily product obtained was isolated by column chromatography (Wako gel C-200, eluted with toluene:ethyl acetate=10:1) to give 0.8 g of the desired product as a colorless oily product.
$n^{24.4}_D$ 1.5677

EXAMPLE 3

Synthesis of dl-5-chloro-6-ethyl-4-($\alpha$-ethyl-4-(4-trifluoromethyl-2,3,5,6-tetrafluorophenoxy)-benzylamino)pyrimidine:

A mixture of 1 g of dl-5-chloro-6-ethyl-4-($\alpha$-ethyl-4-hydroxybenzylamino)pyrimidine, 1 g of perfluorotoluene, 0.24 g of powdery potassium hydroxide and 20 ml of 1,3-dimethyl-2-imidazolidinone (DMI) was heated under stirring at 70° C. for 8 hours. After completion of the reaction, the reaction mixture was poured into water, and extracted with toluene. The extract was washed with water, dried over anhydrous sodium sulfate and then toluene was evaporated under reduced pressure. The oily product obtained was isolated by column chromatography (Wako gel C-200, eluted with toluene:ethyl acetate=30:1) to give 1.5 g of the desired product as colorless crystals.
m.p. 58°-61° C.

EXAMPLE 4

Synthesis of dl-4-(α-ethyl-4-pentafluorophenoxybenzylamino)-quinazoline:

To a solution of 0.52 g of 4-chloroquinazoline, 1.0 g of dl-α-ethyl-4-pentafluorophenoxybenzylamine and 1 ml of triethylamine dissolved in 20 ml of toluene was added a catalytic amount of 4-(N,N-dimethylamino)-pyridine, and the mixture was heated under reflux for 8 hours. After completion of the reaction, the reaction mixture was washed with water, dried over anhydrous sodium sulfate and then toluene was evaporated under reduced pressure. The oily product obtained was isolated by column chromatography (Wako gel C-200, eluted with toluene:ethyl acetate=3:1) to give 0.5 g of the desired product as colorless crystals.

EXAMPLE 5

Synthesis of dl-4-(α-methyl-4-pentafluorophenoxybenzylamino)thieno[2,3-d]pyrimidine:

To a solution of 0.4 g of 4-chlorothieno[2,3-d]pyrimidine, 0.7 g of dl-α-methyl-4-pentafluorophenoxybenzylamine and 1 ml of triethylamine dissolved in 20 ml of toluene was added a catalytic amount of 4-(N,N-dimethylamino)pyridine, and the mixture was heated under reflux for 8 hours. After completion of the reaction, the reaction mixture was washed with water, dried over anhydrous sodium sulfate and then toluene was evaporated under reduced pressure. The oily product obtained was isolated by column chromatography (Wako gel C-200, eluted with toluene:ethyl acetate=3:1) to give 0.4 g of the desired product as colorless crystals. m.p. 158°–161° C.

EXAMPLE 6

Five parts by weight of the compound of Compound No. 1, 35 parts by weight of bentonite, 57 parts by weight of talc, 1 part by weight of Neopelex powder (trade name; manufactured by Kao Atlas) and 2 parts by weight of sodium lignin sulfonate were uniformly mixed, and then kneaded with addition of a small amount of water, followed by granulation and drying to obtain granules.

EXAMPLE 7

Ten (10) parts by weight of the compound of Compound No. 1, 70 parts by weight of kaolin, 18 parts by weight of carbon, 1.5 parts by weight of Neopelex powder (trade name; manufactured by Kao Atlas) and 0.5 part by weight of Demol (trade name: manufactured by Kao Atlas) were uniformly mixed, followed by pulverization to obtain wettable powder.

EXAMPLE 8

To 20 parts by weight of the compound of Compound No. 1 and 70 parts by weight of xylene were added 10 parts by weight of Toxanone (trade name; manufactured by Sanyo Kasei Kogyo), and the mixture was uniformly mixed, and dissolved to obtain an emulsion.

EXAMPLE 9

Five parts by weight of the compound of Compound No. 1, 50 parts by weight of talc and 45 parts by weight of kaolin were uniformly mixed to obtain powder.

EXAMPLE 10

Control activity test (preventive activity) against wheat brown rust

In plastic planting pots of 6 cm in diameter, ten wheats (species: Kobushikomugi) were grown per each pot, and to young plants at the 1.5 leaf stage were sprayed the wettable powder of the respective compounds shown in Table 3 prepared similarly as in Example 7 diluted to 100 ppm with water containing a surfactant (0.01%) in an amount of 20 ml per each pot. After spraying, the plants were cultivated in a glass hothouse for 2 days, and then a wheat brown rust spore suspension ($7 \times 10^4$ spores/ml) was uniformly inoculated by spraying thereon.

After inoculation, the plants were grown in a glass hothouse for one week, and the extent of the wheat brown rust lesion appeared on the first leave was examined. The drug effect was judged by comparison with the extent of the non-treated group. The results are shown in Table 3.

Evaluation is shown by the 6 ranks of 5 to 0, and one without lesion being rated as 5, one with lesion area of 10 or less as compared with the non-treated group as 4, about 20% as 3, about 40% as 2, about 60% as 1, and one which is wholly afflicted with the disease as 0.

As a Control, the following compounds disclosed in Japanese Unexamined Patent Publication No. 225364/1988 were used.

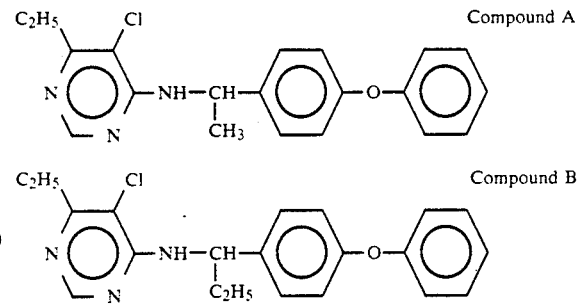

TABLE 3

| Compound No. | Effect |
| --- | --- |
| 1 | 5 |
| 2 | 5 |
| 4 | 3 |
| 6 | 3 |
| 7 | 5 |
| 9 | 5 |
| 10 | 5 |
| 11 | 5 |
| 15 | 3 |
| 16 | 4 |
| 17 | 4 |
| 19 | 2 |
| 21 | 5 |
| 23 | 5 |
| 24 | 5 |
| 25 | 5 |
| 26 | 5 |
| 27 | 5 |
| 28 | 4 |
| 29 | 5 |
| 33 | 5 |
| 36 | 5 |
| 37 | 5 |
| 41 | 5 |
| 42 | 5 |
| Compound A | 0 |
| Compound B | 0 |

TABLE 3-continued

| Compound No. | Effect |
|---|---|
| No treatment | 0 |

EXAMPLE 11

Control activity test (preventive activity) against barley powdery mildew

In plastic planting pots of 6 cm in diameter, ten barleys (species: Black barley) were grown per each pot, and to young plants at the 1.5 leaf stage was sprayed the wettable powder prepared similarly as in Example 7 diluted to 100 ppm with water containing a surfactant (0.01 %) in an amount of 20 ml per each pot. After spraying, the plants were cultivated in a glass hothouse for 2 days, and then barley powdery mildew conidial spores were collected from the afflicted leaves, which were sprayed uniformly on the plants to effect inoculation.

After inoculation, the plants were grown in a glass hothouse for one week, and the extent of the barley powdery mildew lesion appeared on the first leave was examined.

The drug effect was judged by comparison with the extent of the non-treated group. The results are shown in Table 4.

Evaluation is shown by the 6 ranks of 5 to 0, and one without lesion being rated as 5, one with lesion area of 10% or less as compared with the non-treated group as 4, about 20% as 3, about 40% as 2, about 60% as 1, and one which is wholly afflicted with the disease as 0.

As a Control, the same compounds as in Example 10 were used.

TABLE 4

| Compound No. | Effect |
|---|---|
| 1 | 5 |
| 2 | 4 |
| 9 | 5 |
| 10 | 3 |
| 11 | 5 |
| 21 | 5 |
| 23 | 4 |
| 25 | 4 |
| 26 | 4 |
| 28 | 3 |
| 29 | 5 |
| 33 | 5 |
| 36 | 5 |
| 37 | 3 |
| 41 | 5 |
| 42 | 4 |
| Compound A | 0 |
| Compound B | 0 |
| No treatment | 0 |

EXAMPLE 12

Control activity test (preventive activity) against cucumber downy mildew

In plastic planting pots of 6 cm in diameter, one cucumber (species: Sagamihanjiro) was grown per each pot, and to young plants at the 1.5 leaf stage was sprayed the wettable powder prepared similarly as in Example 7 diluted to 500 ppm with water containing a surfactant (0.01%) in an amount of 20 ml per each pot. After spraying, the plants were cultivated in a glass hothouse for 2 days, and then cucumber downy mildew bacterial zoosprangia were prepared from the afflicted leaves, which were sprayed uniformly on the plants to effect inoculation.

After inoculation, after maintained under dark at 20° C. for 2 days, the plants were grown in a glass hothouse for five days, and the extent of the cucumber downy mildew lesion appeared on the first leave was examined. The drug effect was judged by comparison with the extent of the non-treated group. The results are shown in Table 5.

Evaluation is shown by the 6 ranks of 5 to 0, and one without lesion being rated as 5, one with lesion area of 10% or less compared with the non-treated groups as 4, about 20% as 3, about 40% as 2, about 60% as 1, and one which is wholly afflicted with the disease as 0.

As a Control, the same compounds as in Example 10 were used.

TABLE 5

| Compound No. | Effect |
|---|---|
| 1 | 4 |
| 2 | 4 |
| 3 | 4 |
| 9 | 2 |
| 10 | 2 |
| 11 | 3 |
| 13 | 4 |
| 14 | 3 |
| 15 | 5 |
| 17 | 3 |
| 23 | 4 |
| 24 | 2 |
| Compound A | 0 |
| Compound B | 0 |
| No treatment | 0 |

EXAMPLE 13

Control activity test (preventive activity) against rice blast

IN plastic planting pots of 6 cm in diameter, ten rices (species: Nipponbare) were grown per each pot, and to young plants at the 1.5 leaf stage was sprayed the wettable powder prepared similarly as in Example 7 diluted to 500 ppm with water containing a surfactant (0.01%) in an amount of 20 ml per each pot. After spraying, the plants were cultivated in a glass hothouse for 2 days, and then cucumber downy mildew zoosprangia were prepared from the afflicted leaves, which were sprayed uniformly on the plants to effect inoculation.

After inoculation, the plants were grown in a humid chamber of 28° C. for 5 days, and the extent of the rich blast lesion appeared on the first leave was examined. The drug effect was judged by comparsion with the extent of the non-treated group. The results are shown in Table 6.

Evaluation is shown by the 6 ranks o 5 to 0, and one without lesion being rated as 5, one with lesion area of 10% or less as compared with the non-treated group as 4, about 20% as 3, about 40% as 2, about 60% as 1, and one which is wholly afflicted with the disease as 0.

As a Control, the same compounds as in Example 10 were used.

TABLE 6

| Compound No. | Effect |
|---|---|
| 2 | 4 |
| 4 | 5 |
| 8 | 4 |
| 16 | 4 |
| 33 | 5 |
| 37 | 4 |

TABLE 6-continued

| Compound No. | Effect |
|---|---|
| 42 | 5 |
| Compound A | 0 |
| Compound B | 0 |
| No treatment | 0 |

EXAMPLE 14

Activity test against diamondback moth

The compounds shown in Table 1 were formulated into wettable agents similarly as described in Example 7, and each formulation was diluted with water containing a surfactant (0.01%) to 1000 ppm to prepare a chemical solution. In each chemical solution, cabbage leaf strip (5 cm × 5 cm) was dipped for 30 seconds, and placed in a plastic cup. After air drying, ten 3rd instar diamond moth larvae were free, and the plastic cup was closed with a lid and left to sand in a thermostatic chamber of 25° C. Two days later, the numbers of live and dead insects were counted to determine the % mortality. The results are shown in Table 7.

In Table 7, those with mortality of 100% are shown as A, those with 99 to 80% as B, those with 79 to 60% as C and those with not more than 59% as D.

TABLE 7

| Compound No. | Activity against diamond back |
|---|---|
| 1 | A |
| 2 | A |
| 4 | B |
| 6 | A |
| 7 | B |
| 8 | B |
| 9 | A |
| 10 | A |
| 15 | B |
| 21 | A |
| 25 | B |
| 26 | A |
| 33 | A |
| 36 | A |
| 37 | A |
| 42 | B |

EXAMPLE 15

Activity test against green rich leafhopper

The compounds shown in Table 1 were formulated into wettable powder similarly as described in Example 7, and each formulation was diluted with water containing a surfactant (0.01%) to 1000 ppm to prepare a chemical solution. In each chemical solution was dipped young rice seedlings for 30 seconds, and the rice seedlings after air drying were inserted into a glass cylinder. The 4th instar green rice leafhopper larvae were freed into the cylinder, which was then left to stand stoppered with a porous plug in a thermostatic chamber of 25° C. 4 days later, the numbers of a live and dead insects were counted to determine the % mortality.

In Table 8, those with mortality of 100% are shown as A, those with 99 to 80% as B, those with 79 to 60% as C and those with not more than 59% as D.

TABLE 8

| Comp. No. | Activity against green rice leafhopper |
|---|---|
| 1 | A |
| 2 | A |
| 6 | B |
| 8 | A |
| 9 | A |
| 13 | B |
| 15 | A |
| 21 | A |
| 24 | B |
| 26 | A |
| 33 | A |
| 36 | A |

EXAMPLE 16

Synthesis of dl-5-chloro-6-ethyl-4-(α-ethyl-4-trifluoromethoxybenzylamino)pyrimidine (Compound No. 44)

To a solution of 0.9 g of 4,5-dichloro-6-ethylpyrimidine, 1.0 g of dl-α-ethyl-4-trifluoromethoxybenzylamine and 1 ml of triethylamine dissolved in 20 ml of toluene was added a catalytic amount of 4-(N,N-dimethylamino)pyridine, and the mixture was heated under reflux for 8 hours.

After the reaction, the reaction mixture was washed with water, dried over anhydrous sodium sulfate and the toluene was evaporated under reduced pressure. The oily product obtained was isolated by column chromatography (Wako gel C-200, eluted with toluene ethyl acetate=15:1) to give 1.0 g of the desired product as a colorless oily product.

$^1$H-NMR ($\delta$ ppm, CDCl$_3$) 0.96 (3H,t), 1.26 (3H,t), 1.92 (2H,m), 2.79 (2H,q), 5.15 (1H,m), 5.59 (1H,d), 7.10-7.37 (4H,m), 8.37 (1H,s)

EXAMPLE 17

Synthesis of dl-5-chloro-6-ethyl-4-(α-ethyl-4-bromodifluoromethoxybenzylamino)pyrimidine (Compound No. 45)

To a solution of 2.5 g of dl-5-chloro-6-ethyl-4-(-α-ethyl-4-hydroxybenzylamino) pyrimidine dissolved in 25 ml of N,N-dimethylformamide (DMF) was added gradually 0.4 g of 60% sodium hydride stirred at room temperature, followed further by stirring for 5 minutes. Subsequently, a solution of 10 g of bromodifluoromethane dissolved in 20 ml of DMF was added and the reaction was carried out under stirring at room temperature for 24 hours.

After the reaction, the reaction mixture was poured into water, extracted with toluene, the toluene layer was washed with water, dried over anhydrous sodium sulfate and the toluene was evaporated under reduced pressure. The oily product obtained was isolated by column chromatography (Wako gel C-200, eluted with toluene:ethyl acetate=15:1) to give 0.5 g of the desired product as a colorless oily product.

$^1$H-NMR ($\delta$ ppm, CDCl$_3$)

0.97 (3H,t), 1.26 (3H,t), 1.94 (2H,m), 2.79 (2H,q), 5.16 (1H,m), 5.63 (1H,d), 7.20-7.38 (4H,m), 8.37 (1H,s)

EXAMPLE 18

Synthesis of dl-5-chloro-6-ethyl-4-(α-ethyl-4-difluoromethoxybenzylamino)pyrimidine (Compound No. 46)

To a solution of 0.9 g of 4,5-dichloro-6-ethylpyrimidine, 1.0 g of dl-α-ethyl-4-difluoromethoxybenzylamine and 1 ml of triethylamine dissolved in 20 ml of toluene was added a catalytic amount of 4-(N,N-dimethylamino)pyridine, and the mixture was heated under reflux for 8 hours.

After the reaction, the reaction mixture was washed with water, dried over anhydrous sodium sulfate and the toluene was evaporated under reduced pressure. The oily product obtained was isolated by column chromatography (Wako gel C-200, eluted with toluene:ethyl acetate=5:1) to give 1.1 g of the desired product as colorless oily product.

$^1$H-NMR (δ ppm, CDCl$_3$) 0.95 (3H,t), 1.25 (3H,t), 1.92 (2H,m), 2.78 (2H,q), 5.11 (1H,dd), 5.59 (1H,d), 6.49 (1H,t) 7.08–7.34 (4H,m), 8.36 (1H,s)

EXAMPLE 19

Five parts by weight of the compound No. 44, 35 parts by weight of bentonite, 57 parts by weight of talc, 1 part by weight of Neopelex powder (trade name; manufactured by Kao Atlas) and 2 parts by weight of sodium lignin sulfonate were uniformly mixed, and then the mixture was kneaded with addition of a small amount of water, followed by granulation and drying, to obtain granules.

EXAMPLE 20

Ten (10) parts by weight of the compound of Compound No. 44, 70 parts by weight of kaolin, 18 parts by weight of carbon, 1.5 parts by weight of Neopelex powder (trade name; manufactured by Kao Atlas) and 0.5 part by weight of Demol (trade name: manufactured by Kao Atlas) were uniformly mixed, followed by pulverization to obtain wettable powder.

EXAMPLE 21

To 20 parts by weight of the compound of Compound No. 44 and 70 parts by weight of xylene were added 10 parts by weight of Toxanone (trade name; manufactured by Sanyo Kasei Kogyo), and the mixture was uniformly mixed, dissolved to obtain an emulsion.

EXAMPLE 22

Five parts by weight of the compound of Compound No. 44, 50 parts by weight of talc and 45 parts by weight of kaolin were uniformly mixed to obtain powder.

EXAMPLE 23

Control activity test (preventive activity) against wheat brown rust

The tests were conducted in the same manner as in Example 10 except for employing the method of Example 20 as the method for preparation of wettable powder, diluting it to 50 ppm, and using the compounds shown in Table 9 as the compound of the present invention. The evaluation methods used were the same as in Example 10.

As Control, the compound C disclosed in Japanese Unexamined Patent Publication No. 36666/1984 and the compound D disclosed in Japanese Unexamined Patent Publication No. 68362/1989 were used.

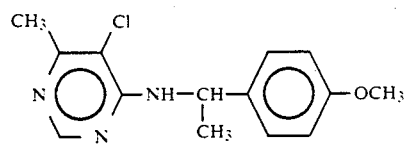

Compound C

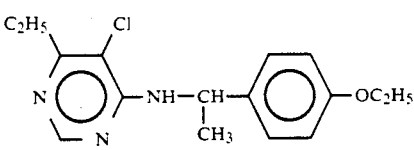

Compound D

TABLE 9

| Compound No. | Effect |
|---|---|
| 44 | 5 |
| 45 | 5 |
| 46 | 5 |
| 47 | 5 |
| 51 | 4 |
| 52 | 4 |
| 53 | 5 |
| 55 | 5 |
| 57 | 4 |
| 61 | 5 |
| 64 | 5 |
| 66 | 5 |
| 67 | 5 |
| 68 | 5 |
| 69 | 4 |
| 70 | 5 |
| 71 | 4 |
| 72 | 5 |
| 73 | 5 |
| 74 | 5 |
| 75 | 3 |
| 76 | 4 |
| 79 | 5 |
| 82 | 4 |
| 84 | 3 |
| 85 | 5 |
| 86 | 5 |
| 87 | 5 |
| 88 | 3 |
| 89 | 5 |
| 90 | 5 |
| 91 | 5 |
| 96 | 4 |
| 97 | 5 |
| 98 | 4 |
| 101 | 5 |
| 102 | 5 |
| Compound C | 1 |
| Compound D | 1 |
| No treatment | 0 |

EXAMPLE 26

Control activity test (preventive activity) against barley powdery mildew

For the compounds of the present invention shown in Table 10, the tests were conducted similarly as in Example 23. The evaluation methods are the same as in Example 11.

As Control, the same compounds C and D as in Example 23 were used.

TABLE 10

| Compound No. | Effect |
|---|---|
| 44 | 5 |
| 45 | 5 |
| 46 | 5 |
| 47 | 5 |
| 51 | 4 |

TABLE 10-continued

| Compound No. | Effect |
| --- | --- |
| 52 | 5 |
| 53 | 5 |
| 55 | 4 |
| 57 | 5 |
| 61 | 5 |
| 62 | 4 |
| 64 | 5 |
| 66 | 5 |
| 67 | 5 |
| 68 | 5 |
| 69 | 4 |
| 70 | 5 |
| 72 | 3 |
| 73 | 3 |
| 74 | 5 |
| 75 | 5 |
| 76 | 5 |
| 79 | 5 |
| 82 | 5 |
| 85 | 5 |
| 86 | 5 |
| 87 | 5 |
| 88 | 4 |
| 89 | 4 |
| 90 | 5 |
| 91 | 5 |
| 92 | 4 |
| 93 | 3 |
| 96 | 5 |
| 97 | 5 |
| 98 | 4 |
| 101 | 5 |
| 102 | 5 |
| Compound A | 0 |
| Compound B | 0 |
| No treatment | 0 |

EXAMPLE 25

Control activity test (preventive activity) against rice blast

In plastic planting pots of 6 cm in diameter, ten rices (species: Nipponbare) were grown per each pot, and to young plants at the 1.5 leaf stage was sprayed the wettable powder prepared similarly as in Example 20 diluted to 500 ppm with water containing a surfactant (0.01%) in an amount of 20 ml per each pot. After spraying, the plants were cultivated in a glass hothouse for 2 days, and then rice blast conidial spores were prepared from the afflicted leaves, which were sprayed uniformly on the plants to effect inoculation.

After inoculation, the plants were grown in a humid chamber of 28° C. for 5 days, and the extent of the rich blast lesion appeared on the first leave was examined. The drug effect was judged by comparison with the extent of the non-treated group.

Evaluation is shown by the 6 ranks of 5 to 0, and one without lesion being rated as 5, one with lesion area of 10% or less as compared with the non-treated group as 4, about 20% as 3, about 40% as 2, about 60% as 1, and one which is wholly afflicted with the disease as 0. The results are shown in Table 11. As Control, the same compounds as in Example 23 were used.

TABLE 11

| Compound No. | Effect |
| --- | --- |
| 44 | 4 |
| 51 | 4 |
| 52 | 5 |
| 57 | 5 |
| 61 | 5 |
| 64 | 5 |

TABLE 11-continued

| Compound No. | Effect |
| --- | --- |
| 66 | 5 |
| 67 | 5 |
| 68 | 5 |
| 69 | 5 |
| 70 | 5 |
| 82 | 5 |
| 83 | 4 |
| 84 | 4 |
| 85 | 4 |
| 86 | 5 |
| 87 | 4 |
| 88 | 4 |
| 89 | 5 |
| 90 | 4 |
| 91 | 4 |
| 92 | 5 |
| 93 | 5 |
| 96 | 5 |
| 97 | 5 |
| 98 | 4 |
| 101 | 4 |
| 102 | 5 |
| Compound C | 1 |
| Compound D | 1 |
| No treatment | 0 |

EXAMPLE 26

Control activity test (preventive activity) against cucumber downy mildew

In plastic planting pots of 6 cm in diameter, one cucumber (species: Sagamihanpaku) was grown per each pot, and to young plants at the 1.5 leaf stage was sprayed the wettable powder prepared similarly as in Example 20 diluted to 500 ppm with water containing a surfactant (0.01%) in an amount of 20 ml per each pot. After spraying, the plants were cultivated in a glass hothouse for 2 days, and then cucumber downy mildew zoosprangia were prepared from the afflicted leaves, which were sprayed uniformly on the plants to effect inoculation.

After inoculation, after maintained under dark at 20° C. for 2 days, the plants were grown in a glass hothouse for five days, and the extent of the cucumber downy mildew lesion appeared on the first leave was examined. The drug effect was judged by comparison with the extent of the non-treated group.

Evaluation is shown by the 6 ranks of 5 to 0, and one without lesion being rated as 5, one with lesion area of 10% or less as compared with the non-treated group as 4, about 20% as 3, about 40% as 2, about 60% as 1, and one which is wholly afflicted with the disease as 0. The results are shown in Table 12. As Control, the same compounds as in Example 23 were used.

TABLE 12

| Compound No. | Effect |
| --- | --- |
| 61 | 5 |
| 75 | 4 |
| 76 | 3 |
| 78 | 3 |
| 79 | 3 |
| 82 | 5 |
| 83 | 3 |
| 85 | 5 |
| 86 | 5 |
| 87 | 4 |
| 88 | 5 |
| 89 | 5 |
| 90 | 5 |
| 91 | 5 |
| 93 | 5 |

TABLE 12-continued

| Compound No. | Effect |
| --- | --- |
| 101 | 5 |
| 102 | 5 |
| Compound A | 1 |
| Compound B | 1 |
| No treatment | 0 |

EXAMPLE 27

Activity test against diamondback moth

The compounds shown in Table 2 were formulated into wettable powder similarly as described in Example 20, and each formulation was diluted with water containing a surfactant (0.01%) to 1000 ppm to prepare a chemical solution. In each chemical solution, cabbage leaf strip (5 cm × 5 cm) was dipped for 30 seconds, and placed in a plastic cup. After air drying, ten 3rd instar diamond moth larvae were freed, and the plastic cup was closed with a lid and left to stand in a thermostatic chamber of 25° C. Two days later, the numbers of a live and dead insects were counted to determine the % mortality. The results are shown in Table 13.

In Table 13, those with mortality of 100% are shown as A, those with 99 to 80% as B, those with 79 to 60% as C and those with not more than 59% as D.

TABLE 13

| Compound No. | Activity against diamond back |
| --- | --- |
| 46 | A |
| 47 | A |
| 61 | A |
| 66 | A |
| 67 | A |
| 68 | A |
| 74 | A |
| 79 | A |
| 82 | A |
| 86 | A |
| 87 | A |
| 88 | A |
| 90 | A |
| 96 | A |
| 97 | A |

EXAMPLE 28

Activity test against brown planthoppers

The compounds shown in Table 2 were formulated into wettable powder similarly as described in Example 20, and each formulation was diluted with water containing a surfactant (0.01%) to 1000 ppm to prepare a chemical solution. In each chemical solution, rice young seedling was dipped for 30 seconds. After air drying, it was placed in a glass cylinder and ten 3rd brown planthoppers were freed, and the plastic cup was closed with a porous stopper and left to stand in a thermostatic chamber of 25 .C Four days later, the numbers of a live and dead insects were counted to determine the % mortality. The results are shown in Table 14.

In Table 14, those with mortality of 100% are shown as A, those with 99 to 80% as B, those with 79 to 60% as C and those with not more than 59% as D.

TABLE 14

| Compound No. | Activity against brown planthopper |
| --- | --- |
| 46 | A |
| 47 | A |
| 61 | A |
| 66 | A |
| 67 | A |
| 68 | A |
| 74 | A |
| 75 | A |
| 76 | A |
| 79 | A |
| 82 | A |
| 85 | A |
| 86 | A |
| 87 | A |
| 90 | A |
| 96 | A |
| 97 | A |

EXAMPLE 29

Activity test against female adult of two spotted spider mite

The compounds shown in Table 2 were formulated into wettable powder similarly as described in Example 20, and each formulation was diluted with water containing a surfactant (0.01%) to 1000 ppm to prepare a chemical solution. In each chemical solution, a kidney bean leaf (20 mm in diameter) was dipped for 10 seconds.

After air drying, it was placed in a glass cylinder and ten female adult of two spotted spider mites were freed, and the plastic cup was closed with a porous stopper and left to stand in a thermostatic chamber of 25 .C Three days later, the numbers of a live and dead insects were counted to determine the % mortality of mites. The results are shown in Table 15.

In Table 15, those with mortality of 100% are shown as A, those with 99 to 80% as B, those with 79 to 60% as C and those with not more than 59% as D.

TABLE 15

| Comp. No. | Activity against two spotted spider mite |
| --- | --- |
| 46 | A |
| 47 | A |
| 57 | A |
| 61 | A |
| 62 | A |
| 66 | A |
| 67 | A |
| 68 | A |
| 74 | A |
| 75 | A |
| 78 | A |
| 79 | A |
| 82 | A |
| 86 | A |
| 87 | A |
| 90 | A |

The compounds having fluoromethoxy group of the present invention have by far superior fungicidal effect as compared with analogous compounds having methoxy group.

We claim:

1. A compound of the formula (I) or an acid addition salt thereof:

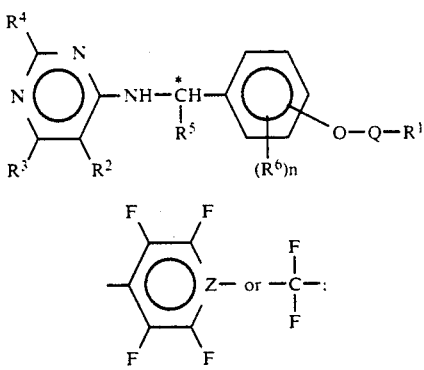

wherein Q represents represents hydrogen atom, a halogen atom, a halo-lower alkyl group, an alkanoyl group, nitro group, cyano group or 1,3-dioxoran-2-yl group; $R^2$ and $R^3$ each represent a halogen atom or a lower alkyl group, or $R^2$ and $R^3$ are fused together with the pyrimidine ring to which they are bonded to represent an unsaturated 5-or 6-membered ring which may also have one sulfur atom constituting the ring; $R^4$ represents hydrogen atom, a halogen atom, a lower alkyl group, a cycloalkyl group, a lower alkoxy group, a lower alkylthio group or an amino group which may be substituted with a lower alkyl; $R^5$ represents hydrogen atom, a lower alkyl group, a cycloalkyl group or a halo-lower alkyl group; $R^6$ represents hydrogen atom, a halogen atom, a lower alkyl group, a lower alkoxy group, a halo-lower alkoxy group; n represents an integer of 1 or 2 and Z represents carbon atom or nitrogen atom.

2. The compound according to claim 1, wherein $R^1$ is at least one selected from the group consisting of hydrogen, fluorine, chlorine, bromine, iodine, trifluoromethyl group, difluoromethyl group, 2-fluoromethyl group, 2,2,2-trifluoroethyl group, formyl group, acetyl group, propionyl group, butyryl group, isobutyryl group, valeryl group, nitro group, cyano group and 1,3-dioxoran-2-yl group.

3. The compound according to claim 2, wherein $R^1$ is at least one selected from the group consisting of hydrogen, fluorine, chlorine, bromine, trifluoromethyl group, difluoromethyl group and formyl group.

4. The compound according to claim 1, wherein $R^2$ and $R^3$ are each at least one selected from the group consisting of fluorine, chlorine, bromine, iodine, methyl group, ethyl group, propyl group, isopropyl group, butyl group, isobutyl group, sec-butyl group, t-butyl group, pentyl group, isopentyl group and neopentyl group.

5. The compound according to claim 4, wherein $R^2$ is at least one selected from the group consisting of fluorine, chlorine, bromine, methyl group and ethyl group.

6. The compound according to claim 4, wherein $R^3$ is at least one selected from the group consisting of methyl group, ethyl group and propyl group.

7. The compound according to claim 1, wherein $R^4$ is at least one selected from the group consisting of hydrogen, fluorine, chlorine, bromine, iodine, methyl group, ethyl group, propyl group, isopropyl group, butyl group, isobutyl group, sec-butyl group, t-butyl group, pentyl group, isopentyl group, neopentyl group, cyclopropyl group, cyclopentyl group, cyclohexyl group, methoxy group, ethoxy group, propoxy group, isopropoxy group, butoxy group, pentyloxy group, methylthio group, ethylthio group, propylthio group, isopropylthio group, butylthio group, pentylthio group, amino group, monomethylamino group, dimethylamino group, monoethylamino group, diethylamino group, monopropylamino group, dipropylamino group, monobutylamino group, dibutylamino group, monopentylamino group and dipentylamino group.

8. The compound according to claim 7, wherein $R^4$ is at least one selected from the group consisting of hydrogen and methyl group.

9. The compound according to claim 1, wherein $R^5$ is at least one selected from the group consisting of hydrogen, methyl group, ethyl group, propyl group, isopropyl group, butyl group, isobutyl group, sec-butyl group, t-butyl group, pentyl group, isopentyl group, neopentyl group, cyclopropyl group, cyclopentyl group, cyclohexyl group, monofluoromethoxy group, difluoromethoxy group, trifluoromethoxy group, bromofluoromethoxy group, 2-fluoroethoxy group, 2,2-difluoroethoxy group, 2,2,2-trifluoroethoxy group and 3,3,3-trifluoropropoxy group.

10. The compound according to claim 9, wherein $R^5$ is at least one selected from the group consisting of methyl group, ethyl group, isopropyl group and cyclopropyl group.

11. The compound according to claim 1, wherein $R^6$ is at least one selected from the group consisting of hydrogen, fluorine, chlorine, bromine, iodine, methyl group, ethyl group, propyl group, isopropyl group, butyl group, isobutyl group, sec-butyl group, t-butyl group, pentyl group, isopentyl group, neopentyl group, methoxy group, ethoxy group, propoxy group, isopropoxy group, butoxy group, pentyloxy group, monofluoromethoxy group, difluoromethoxy group, trifluoromethoxy group, bromodifluoromethoxy group, 2-fluoroethoxy group, 2,2-difluoroethoxy group, 2,2,2-trifluoroethoxy group and 3,3,3-trifluoropropoxy group.

12. The compound according to claim 11, wherein $R^6$ is at least one selected from the group consisting of hydrogen, fluorine, chlorine, methyl group, methoxy group and difluoromethoxy group.

13. The compound according to claim 1, wherein the substitution position of Q is at the 3-position or 4-position relative to $>CH-R^5$.

14. The compound according to claim 1, wherein the compound is 5-chloro-6-ethyl-4-(α-ethyl-4-pentafluorophenoxybenzylamino)pyrimidine.

15. The compound according to claim 1, wherein the compound is 5-chloro-6-ethyl-4-(α-methyl-4-pentafluorophenoxybenzylamino)pyrimidine.

16. The compound according to claim 1, wherein the compound is 5-chloro-6-methyl-4-(α-ethyl-4-pentafluorophenoxybenzylamino)pyrimidine.

17. The compound according to claim 1, wherein the compound is 5-chloro-6-methyl-4-(α-ethyl-4-pentafluorophenoxybenzylamino)pyrimidine.

18. The compound according to claim 1, wherein the compound is 5-fluoro-6-methyl-4-(α-methyl-4-pentafluorophenoxybenzylamino)pyrimidine.

19. The compound according to claim 1, wherein the compound is 5-fluoro-6-methyl-4-(α-ethyl-4-pentafluorophenoxybenzylamino)pyrimidine.

20. The compound according to claim 1, wherein the compound is 6-ethyl-5fluoro-4-(α-methyl-4-pentafluorophenoxybenzylamino)pyrimidine.

21. The compound according to claim 1, wherein the compound is 5-chloro-6-ethyl-4-(α-ethyl-4-trifluoromethyoxybenzylamino)pyrimidine.

22. The compound according to claim 1, wherein the compound is 5-chloro-6-ethyl-4-(α-ethyl-4-bromodifluoromethoxybenzylamino)pyrimidine.

23. The compound according to claim 1, wherein the compound is 5-chloro-6-ethyl-4-(α-ethyl-4-difluoromethoxybenzylamino)pyrimidine.

24. The compound according to claim 1, wherein the compound is 5-chloro-6-methyl-4-(α-ethyl-4-difluoromethoxybenzylamino)pyrimidine.

25. The compound according to claim 1, wherein the compound is 5-fluoro-6-methyl-4-(α-methyl-4-difluoromethoxybenzylamino)pyrimidine.

26. The compound according to claim 1, wherein the compound is 5-fluoro-6-methyl-4-(α-ethyl-4-difluoromethoxybenzylamino)pyrimidine.

27. The compound according to claim 1, wherein the compound is 6-ethyl-5fluoro-4-(α-methyl-4-difluoromethoxybenzylamino)pyrimidine.

28. The compound according to claim 1, wherein the compound is 5-chloro-6-methyl-4-(α-methyl-4-difluoromethoxybenzylamino)pyrimidine.

29. The compound according to claim 1, wherein the compound is 5-chloro-6-ethyl-4-(α-methyl-4-difluoromethoxybenzylamino)pyrimidine.

30. The compound according to claim 1, wherein the compound is 5-chloro-6-methyl-4-(α-methyl-3,4-bis(difluoromethoxy)-benzyl-amino)pyrimidine.

31. The compound according to claim 1, wherein the compound is 5-chloro-6-ethyl-4-(α-methyl-3,4-bis(difluoromethoxy)benzylamino)pyrimidine.

32. A fungicidal composition comprising a fungicidally effective amount of a compound of the formula (I) or an acid addition salt thereof as defined in claim 1 as the active ingredient in admixture with a carrier.

33. The fungicide composition according to claim 32, wherein the compound is a compound selected from the group consisting of 5-chloro-6-ethyl-4-(α-ethyl-4-pentafluorophenoxybenzylamino)pyrimidine; 5-chloro-6-ethyl-4-(α-methyl-4-pentafluorophenoxybenzylamino)-pyrimidine; 5-chloro-6-methyl-4-(α-ethyl-4-pentafluorophenoxybenzylamino)-pyrimidine; 5-chloro-6-methyl-4-(α-methyl-4-pentafluorophenoxybenzylamino)-pyrimidine; 5-fluoro-6-methyl-4-α-methyl-4-pentafluorophenoxybenzylamino)pyrimidine; 5-fluoro-6-methyl-4-(α-ethyl-4-pentafluorophenoxybenzylamino)pyrimidine; 6-ethyl-5-fluoro-4-(α-methyl-4-pentafluorophenoxybenzylamino)pyrimidine; 5-chloro-6-ethyl-4-trifluoromethoxybenzylamino)pyrimidine; 5-chloro-6-ethyl-4-(α-ethyl-4-bromodifluoromethoxybenzylamino)pyrimidine; 5-chloro-6ethyl-4-(α-ethyl-4-difluoromethoxybenzylamino)pyrimidine; 5-chloro-6-methyl-4-(α-ethyl-4-difluoromethoxybenzylamino)pyrimidine; 5-fluoro-6-methyl-4-(α-methyl-4-difluoromethoxybenzylamino)pyrimidine; 5-fluoro-6-methyl-4-(α-ethyl-4-difluoromethoxybenzylamino)pyrimidine; 6-ethyl-5-fluoro-4-(α-methyl-4-difluoromethoxybenzylamino)pyrimidine; 5-chloro-6-methyl-4-(α-methyl-4-difluoromethoxybenzylamino)pyrimidine; 5-chloro-6-ethyl-4-(α-methyl-4-difluoromethoxybenzylamino)pyrimidine; 5-chloro-6-methyl-4-(α-methyl-3,4-bis(difluoromethoxy)benzylamino)pyrimidine and 5-chloro-6-ethyl-4-(α-methyl-3,4-bis(difluoromethoxy)benzylamino)pyrimidine.

34. A method of combatting fungi comprising applying a fungicidally effective amount of a compound of the formula (I) or an acid addition salt thereof as defined in claim 1 to fungi or to a locus thereof containing fungi.

35. The method according to claim 34, wherein the compound is selected form the group consisting of 5-chloro-6-ethyl-4-(α-ethyl-4-pentafluorophenoxybenzylamino)pyrimidine; 5-chloro-6-ethyl-4-(α-methyl-4-pentafluorophenoxybenzylamino)-pyrimidine; 5-chloro-6-methyl-4-(α-ethyl-4-pentafluorophnoxybenzylamino)-pyrimidine; 5-chloro-6-methyl-4(α-methyl-4-pentafluorophenoxybenzylamino)pyrimidine; 5-fluoro-6-methyl-4-(α-ethyl-4-pentafluorophenoxybenzylamino)pyrimidine; 6-ethyl-5-fluoro-4-(α-methyl-4-ethyl-4-(α-ethyl-4-trifluoromethoxybenzylamino)-pyrimidine; 5-chloro-6-ethyl-4-(α-ethyl-4-bromodifluoromethoxy benzylamino)pyrimidine; 5-chloro-6-ethyl-4-(α-ethyl-4-difluoromethoxybenzylamio)pyrimidine; 5-chloro-6-methyl-4-(α-ethyl-4-difluoromethoxybenzylamino)pyrimidine; 5-fluoro-6-methyl-5-(α-methyl-4-difluoromethoxybenzylamino)pyrimidine; 5-fluoro-6-methyl-4-(α-ethyl-4-difluoromethoxybenzylamino)pyrimidine; 6-methyl-4-(α-ethyl-4-difluoromethoxybenzylamino)pyrimidine; 6-ethyl-5-fluoro-4-(α-methyl-4difluoromethoxybenzylamino)-pyrimidine; 5-chloro-6-methyl-4-(α-methyl-4difluoromethoxybenzylamino)pyrimidine; 5-chloro-6-methyl-4-(α-methyl-3,4-bis(difluoromethoxy)benzylaminolpyrimidine and 5-chloro-6-ethyl-4-(α-methyl-3,4-bis(difluoromethoxy)-benzylamino)pyrimidine.

36. The method according to claim 34, wherein the fungus is selected from the group consisting of rice blast, cucumber downy mildew, tomato late blight, wheat brown rust and barley powdery mildew.

* * * * *